United States Patent [19]

Levene et al.

[11] Patent Number: 5,179,955
[45] Date of Patent: * Jan. 19, 1993

[54] METHOD OF ABDOMINAL ULTRASOUND IMAGING

[75] Inventors: Harold B. Levene, San Diego; James L. Barnhart, Encinitas; Kenneth J. Widder, Del Mar, all of Calif.

[73] Assignee: Molecular Biosystems, Inc., San Diego, Calif.

[*] Notice: The portion of the term of this patent subsequent to Apr. 28, 2009 has been disclaimed.

[21] Appl. No.: 706,323

[22] Filed: May 28, 1991

Related U.S. Application Data

[63] Continuation-in-part of Ser. No. 660,349, Feb. 22, 1991.

[51] Int. Cl.$^5$ .............................................. A61B 8/00
[52] U.S. Cl. .................................. 128/662.02; 424/11
[58] Field of Search ..................... 128/660.01, 662.02; 424/4, 11

[56] References Cited

U.S. PATENT DOCUMENTS 4,276,885  7/1981  Tickner et al. ................ 128/662.02
4,466,442  8/1984  Hilmann et al. ............ 128/662.02 X
4,774,958  10/1988 Feinstein ...................... 128/660.01
4,957,656  9/1990  Cerny et al. ................ 128/662.02 X

OTHER PUBLICATIONS

Madsen, E. L. et al "Tissue Mimicking Materials for Ultrasound Phantoms" Med. Physics 5(5) Sep.–Oct. 1978, pp. 391–394.
Sommer, F. G. et al "A Phantom For Imaging Biological Fluids" UTS in Med & Biol. vol. 6 No. 2 pp. 135–140 (1980).
Ophir et al., Ultrasound in Med. & Biol., (1989), 15:319–333.
Parker et al., Ultrasound in Med. & Biol.(1987), 13:555–566.

*Primary Examiner*—Francis Jaworski
*Attorney, Agent, or Firm*—Tilton, Fallon, Lungmus & Chestnut

[57] ABSTRACT

Abdominal ultrasound imaging is carried out by oral or rectal administration of an aqueous imaging agent containing micron size clay particles together with a sufficient amount of a solubilized hydrocolloid to maintain the particles in suspension. The walls of the stomach, duodenum and colon become coated with the clay particles and are thereby more clearly delineated by the ultrasonic imaging beam. At the same time, ultrasonic waves partially pass through the walls and delineate structures outside thereof. Wall delineation and wall transparency can thereby be simultaneously achieved.

14 Claims, No Drawings

METHOD OF ABDOMINAL ULTRASOUND IMAGING

RELATED APPLICATION

This application is a continuation-in-part of co-pending application Ser. No. 07/660,349, filed Feb. 22, 1991.

FIELD OF INVENTION

This invention relates to ultrasonic imaging of the human body for diagnostic purposes; and, more particularly, to ultrasonic imaging agents for use in the gastrointestinal tract from the stomach through the large bowel.

BACKGROUND OF INVENTION

An examination procedure known as ultrasonography or sonography is used clinically to delineate bodily structures by ultrasonic imaging. But progress and practical applications of diagnostic ultrasonic imaging have been delayed by the lack of effective clinically usable imaging agents. This is especially the case with respect to ultrasonic imaging agents for the gastrointestinal tract.

Ultrasonic imaging utilizes an ultrasonic scanner to generate and receive sound waves. The scanner is placed on a body surface overlying the area to be imaged, and sound waves are directed toward that area. The scanner detects reflected sound wave and translates that data into images. When ultrasonic energy propagates through an inhomogeneous substance, the acoustic properties of the substance determine the degree of absorption, scattering, and transmission of the ultrasound. As ultrasound waves propagate through one medium to another, there is some degree of reflection at the interface. The degree of reflection is related to the acoustic properties of each material, which properties are determined primarily by the material's density and the speed of sound transmission through the material.

Contrast agents for diagnostic ultrasound were reviewed by Ophir and Parker, *Ultrasound in Med. & Biol.* (1989), 15:319–333. Various contrast agents are described for intravascular administration and imaging. These include free and encapsulated gas bubbles, colloidal suspensions, emulsions, and aqueous solutions. Different mechanisms which can enhance image contrast are discussed; namely, backscatter contrast, attenuation contrast, and speed of sound contrast. Orally administrable ultrasound contrast agents are not discussed. With respect to the development of parenteral imaging agents, the authors observed that the development "has been slow and sporadic, and to date there are no completely satisfactory materials for clinical imaging." In the concluding paragraph, the authors added: "The clinical need for ultrasound contrast agents is high, but much interdisciplinary research, covering acoustic material properties, imaging, biochemistry, histology, toxicology and related specialties will be required before ultrasound contrast agents are commercially available and in routine clinical use."

Particulate suspensions have been used as vascular contrast agents in radiography. For this purpose, radiopaque particles are employed. A particulate contrast-material is described by Parker et al., *Ultrasound in Med. & Biol.* (1987), 13:555–566. The agent proposed for intravenous injection consisted of an iodipamide ethyl ester in the form of dense, relatively incompressible solid collagen particles. A theoretical description of backscatter versus particle size is found in Morse and Ingard, "Theoretical Acoustics", 1986, (Princeton University Press, Princeton, N.J.). It was proposed that such particles might enhance the ultrasound image by relative motion attenuation and/or backscatter attenuation.

SUMMARY OF INVENTION

The ultrasound imaging agents for use in the method of this invention comprise aqueous dispersions of hydrous edible clay particles. The clay particles are preferably sized below 10 microns, such as an average size of 1 to 3 microns. The concentration of the clay particles is important to obtain delineation of the inner walls of the stomach and intestines while permitting part of the ultrasound waves to penetrate through the clay particle-coated walls for examining structures outside of the stomach and intestines. For example, dispersions containing from 1 to 5 grams of clay particles per 100 milliliters of water can be used, providing the particles are maintained in dispersion for introduction into the portion of the gastrointestinal tract associated with the abdominal region to be examined. The dispersions contain solubilized hydrocolloid in an amount sufficient to maintain the clay particles is suspension during their introduction into the GI tract. For example, the dispersions may contain from 1 to 5 grams of solubilized hydrocolloid per 100 milliliters of water. As an example of a presently preferred formulation, 2.5 grams of kaolin particles are dispersed per 100 milliliters of water together with 2.5 grams of water soluble pectin.

When administered orally a coating of clay particles can be formed on the inside of the stomach walls and the inside of the walls of the duodenum. When administered rectally the inner walls of the colon (large bowel) can be coated. The clay particles thus deposited as a coating on the inner walls of the GI tract will reflect part of the ultrasound waves, thereby delineating the walls and any abnormal structures associated with the insides of the walls. However, the deposited coating is not opaque to the sound waves. Rather the coating permits part of the sound waves to pass therethrough so that structures outside of the walls can also be viewed. Wall delineation and wall transparency can thereby be simultaneously obtained.

Other functions can be achieved by the contrast agents of this invention. The contrast agents tend to displace bowel gas, and preferably contains a surface active agent to promote the elimination of gas. The contrast agents disperse essentially homogeneously in the stomach. The relative movement of contrast agent within the stomach as compared to the static stomach wall assists in visualizing the wall. Furthermore, because of the coating action, the stomach wall can be better visualized even after the bulk of the contrast agent has left the stomach.

Another aspect of the present invention involves visualization of the dynamic function of the stomach. While the contrast agent is within the stomach, motility of the stomach during peristalsis can be observed. Such visualization of the dynamic function of the stomach can assist in delineating blockages within the stomach.

DETAILED DESCRIPTION

The imaging dispersions used in the method of this invention contain hydrous edible clay particles as a key ingredient. Clays are natural substances which comprise aluminum silicates that can be readily hydrated by absorption of water. The clays are used in a purified form, suitable for human consumption. They include the clays which are known to be safe for oral administration to humans. For example, such clays as kaolin and bentonite are GRAS-approved for oral administration.

Clay minerals may contain magnesium in addition to aluminum, that is, certain clays are chemically magnesium-aluminum silicates. Natural clays may contain one or more clay minerals. For example, the principle component of kaolin is kaolinite, while the principle component of bentonite is montmorillonite. Fuller's earth, contains both montmorillonite and attapulgite. Preferred clays for use in the imaging agents of the present invention include kaolin, kaolinite, bentonite, montmorillonite, Fuller's earth and attapulgite.

Natural clay particles of the kinds indicated are sized below 30 microns, and preferably below 10 microns. Optimized clays have average particles sizes in the range from 1 to 3 microns. The use of particles of such small micron size is believed to be important in obtaining the novel imaging results of the method of this invention.

In preparing dispersions for the method of this invention, the concentration of the clay may be varied depending on the relative degrees of opacity or delineation with transparency which it is desired to impart to the inner walls of the stomach and the intestines. In general, a concentration should be selected which permits part of the ultrasonic waves to pass through the coated walls of the stomach or small bowel. It is believed that the desired results can be obtained with concentrations ranging from about 0.1 to 10 grams of clay particles per 100 milliliters (ml) of water. In preferred embodiments, 1 to 5 grams of clay particles are dispersed per 100 ml of water. Although the optimum concentrations will vary depending on the abdominal region to be examined and the method of administration (orally or rectally), concentrations of from 2 to 4 grams of clay particles per 100 ml ar believed to be especially desirable.

For achieving the results of the method of this invention, the clay particles preferably are substantially homogeneously dispersed in the aqueous imaging agent. It is therefore desirable to employ a dispersing and suspending agent, which, for the purpose of the present invention is preferably water-solubilized hydrocolloid. Natural hydrocolloids such as pectin are especially desirable. For example, apple pectin or citrus pectin are preferred hydrocolloids. The fruit pectins are available in water soluble form, and therefore are easily solubilized in the imaging agents. Many water-soluble hydrocolloids can be used. If required, the hydrocolloid can be heated to obtain water solubilization. Natural hydrocolloids are a preferred class. Such hydrocolloids in addition to pectin include for example, gum ghatti, gum guar, locust bean gum, tragacanth gum, xanthan gum, arabic gum, carageenen, and agar.

A sufficient amount of the solubilized hydrocolloid is employed to disperse the particulate clay particles so that a relatively homogeneous suspension of the particles is maintained during their introduction into the GI tract. In general, from about 0.1 to 10 grams of hydrocolloid should be employed per 100 ml water. In preferred formulations, as thus far developed, from 1 to 5 grams of a hydrocolloid, such as soluble pectin is employed.

Since the clay particles are in hydrated form, they provide some viscosity to the dispersions, depending on the concentrations used. The hydrocolloid component in addition to being acted as dispersing and suspending agent also acts as a viscosifier. The viscosity of the dispersions can be adjusted by increasing or decreasing the clay particle concentration, and/or increasing or decreasing hydrocolloid concentration.

Although the viscosity of the imaging agents may vary. For example, the viscosity can be in the range from about 10 to 2500 centipoises as determined by standard viscosity test procedures. As thus far developed, preferred embodiments of the imaging agents have viscosities in the range from 100 to 1500 centipoises. The viscosity of the imaging agent is important in assuring rapid effective coating of the inner walls of the stomach or intestines while at the same time avoiding either too brief or an unduly long transit time.

In addition to the ingredients referred to above, the dispersions may contain other ingredients to improve pallatability. For example, the dispersions may contain sweetening agents and/or flavoring agents. Additionally, other ingredients may be added to enhance the degassing effect of the agent, for example by including a surface active agent such as simethicone.

For introduction into the GI tract, whether orally or anally, it is preferred that the suspensions be in sterile form. After preparation, the dispersions can be subjected to heat sterilization but sterilization procedures should be avoided which tend to agglomerate the particles.

The preparations may be administered orally by the patient drinking a prescribed quantity of the dispersion. Alternatively, the suspension can be administered by rectal enema. The amounts to be administered will depend on the imaging purpose, but, in general, the amounts will range from 50 to 1000 ml (0.05 to 1 liters). Clinical doses for most purposes are expected to be in the range from about 100 to 500 ml (0.1 to 0.5 liters).

Ultrasonic imaging can be carried out by standard procedures using commercially available equipment. For use with the dispersion of this invention, the frequency of the ultrasonic beam can be varied, for example from 1 to 10 MHz. For imaging of the GI tract, it is believed that effective enhancement can be obtained in the range from 2 to 6 MHz, which corresponds with typical frequencies for abdominal examinations (e.g. 3 to 5 Mhz).

The imaging agent may be administered orally for examination of the stomach, the upper portions of the small intestines, including the duodenum and jejunum. Rectal administration can be used for examining sections of the large intestines. The imaging may be carried out as soon as the imaging agent has reached the section of the GI tract to be examined. However, the imaging is preferably delayed somewhat. The examination can be carried out with the imaging agent as a coating on the stomach and colon walls. It is believed that useful examinations can be made in a short as time as five minutes and up to 120 minutes. However, most examinations will probably be carried out within 30 minutes after the administration of the imaging agent.

The imaging agent can be used to displace the air in the stomach or sections of the colon. Trapped air volumes can substantially block ultrasonic wave transmission. When the imaging agent replaces the air in a cavity, such as the stomach, increased penetration of the ultrasound waves can be obtained. This together with the wall transparency effect of the imaging agent make it possible to see through the stomach or intestinal walls. For example, this technique may be used to improve ultrasonic examinations of the pancreas through the stomach walls.

The method of this invention and the results that can be obtained thereby are further illustrated in the following experimental examples.

EXAMPLE I

An experimental imaging agent was prepared from sterile water, citrus pectin, and purified edible kaolin. The citrus pectin was water-soluble and the kaolin had an average particle size of from 1 to 2 microns. A premeasured amount of water, such as 500 ml, was added to a Waring blender, and 2.5 grams of kaolin and 2.5 grams of the pectin was added per each 100 ml water. The kaolin can be added first and then the pectin. The blender was turned on to a low speed pulse so that the mixture was blended for at least 10 seconds. The resulting mixture was manually stirred and blended again with the full speed pulse of the blender for at least an additional 10 seconds. The viscosity of the mixture is measured at around 1200 centipoises. The resulting dispersion is then poured through several layers of U.S.P. Gauze and then degassed for a minimum of half an hour. A final viscosity measurement is made to determine if the viscosity is as desired.

The imaging agent thus prepared as described was administered orally to several subjects for ultrasonic imaging of the stomach and upper colon. Observations made during the abdominal ultrasound imaging are summarized as follows:

(1) Precontrast: This was variable from individual to individual, or for a single individual from one day to another, but gas present in the abdomen is not a unusual occurrence. For individuals without a substantial amount of gas, the stomach can be visualized, but the lining of the stomach wall is not well delineated. The pancreas may be imaged, but, in general, the image quality is poor and just the tail portion is observed.

(2) During Administration: Subjects imaged had fasted for a minimum of nine hours prior to examination. Subjects drank approximately 100-200 ml of the above-described contrast agent dispersion. Imaging was essentially continuous from the precontrast time, through the administration, and until the postcontrast visualization was completed.

(3) Postcontrast: As the dispersion entered the stomach, a concentrated bright clump appeared so that a homogeneous contrast was observed in the stomach cavity. In response to the ingestion, the stomach dilated. The contrast in the stomach was very homogeneous and did not contain individual, bright, specular reflectors. The contrast material remained in the stomach for a period of time depending on the viscosity: very quickly (1-2 minutes) for low viscosity solutions (25 to 75 centipoise), and longer (up to 20 minutes) for higher viscosity solutions (200 to 1000 centipoise). As stomach motility occurred, the contrast agent moved within the stomach, giving delineation of the stomach wall. As the contrast material is seen to move out of the stomach, visualization of the pyloric valve and duodenum was provided. Although the stomach then had an empty interior, the lining of the stomach remained coated with the clay particle sound reflectors which gave very good visualization of the wall lining. This effect lasted for some time after the stomach appeared empty (viz. up to 60 minutes). Beginning with the contrast agent entering the stomach, the gas was displaced and there was visualization of structure hidden by the stomach, especially the pancreas. As the contrast material passed out of the stomach and on to further GI structures, the head of the pancreas was visualized.

In a comparable abdominal imaging with a contrast agent that did not contain any pectin, but only kaolin, revealed that the contrast agent did not persist in the stomach and did not coat the stomach lining. The kaolin only contrast agent did not displace bowel gas and did not improve visualization of structures proximal to the stomach. Abdominal imaging with a contrast agent that does not contain any kaolin, but only pectin, revealed that the contrast agent did not provide homogeneous scatterers (the clay particles) within the stomach, and after the agent had left the stomach, the lining of the stomach was not enhanced.

Summarizing, by the use of the contrast agent of this invention there is created an improved acoustic window through the stomach to identify structures hidden by the stomach, e.g., pancreas. This effect was achieved by the removal of intestinal gas and the delineation of structures. At the same time, the coated walls were partially transparent to the ultrasonic waves.

EXAMPLE II

Further studies were made in which imaging agents were prepared as described in Example I except that apple pectin was substituted for citrus pectin, and/or bentonite was substituted for kaolin. The amounts employed of the pectin and bentonite were the same as described in Example I. These imaging agents were tested as described in Example I, and the results obtained were essentially the same as described in Example I.

EXAMPLE III

A complete formulation for practicing the present invention is illustrated by the following.

Water is heated to 77° C. and put into the blender. At the low speed of the blender, 1.7 grams citrus pectin per 100 milliliter water is slowly added into the middle of the vortex and then 2.5 grams kaolin per 100 milliliter water is added. The solution is allowed to cool to room temperature, at which 0.2 grams of an emulsion of the flavoring and defoaming agent per 100 milliliters solution is added.

The emulsion of the flavoring and defoaming agent is prepared in the following manner. In a blender, 1.4 grams sodium saccharin is added to 81.6 milliliters of warm water and mixed until the saccharin is dissolved. To this solution is added 10.0 grams of gum arabic substitute, containing corn syrup solids and modified food starch, followed by mixing until dissolution. Then 0.1 grams of a solution of 1% Dow Corning Antifoam A compound in propylene glycol is added, followed by mixing. The blender is then turned on to high speed and 6.9 grams of artificial wild cherry flavor 2540FD is slowly added and the mixing is continued until the emulsion is homogeneous, a period of about 20 minutes.

We claim:

1. In a method of abdominal ultrasound imaging, the steps comprising: introducing an aqueous dispersion of hydrous edible clay particles into a portion of the gastrointestinal (GI) tract associated with the abdominal region to be examined, said clay particles being sized below 10 microns and said dispersion containing from 0.1 to 10 grams of the particles per 100 milliliters of water together with a sufficient amount of a solubilized hydrocolloid to maintain the particles in suspension during said introduction; and, after said dispersion has coated the GI tract walls in said region, applying an ultrasonic imaging beam to said region to delineate said walls and structures outside thereof.

2. The method steps of claim 1 in which said edible clay is kaolin and said hydrocolloid is pectin.

3. The method steps of claim 1 or claim 2 in which said dispersion contains from 0.1 to 10 grams of hydrocolloid per 100 milliliters of water.

4. The method steps of claim 1 or claim 2 in which said dispersion has a viscosity of from 10 to 2500 centipoise.

5. In a method of abdominal ultrasound imaging, the steps comprising: introducing an aqueous dispersion of hydrous edible clay particles into a portion of the gastrointestinal (GI) tract associated with the abdominal region to be examined, said clay particles being sized below 10 microns and being selected from the group consisting of kaolin, kaolinite, bentonite, montmorillonite, Fuller's earth, and attapulgite, said dispersion containing from 0.1 to 10 grams of the particles per 100 milliliters of water together with a sufficient amount of a solubilized hydrocolloid to maintain the particles in suspension during said introduction, said aqueous dispersion having a viscosity in the range from 10 to 2500 centipoise; and, after said dispersion has coated the GI tract walls in said region, applying an ultrasonic imaging beam to said region to delineate said walls and structures outside thereof.

6. The method steps of claim 5 in which said edible clay is kaolin and said hydrocolloid is pectin.

7. The method steps of claims 5 or 6 in which said dispersion contains from 0.1 to 10 grams of hydrocolloid per 100 milliliters of water.

8. In a method of abdominal ultrasound imaging, the steps comprising: introducing an aqueous dispersion of hydrous edible clay particles into a portion of the gastrointestinal (GI) tract associated with the abdominal region to be examined, said clay particles being sized below 5 microns and said dispersion containing from 1 to 5 grams of the particles per 100 milliliters of water together with 1 to 5 grams of a solubilized hydrocolloid per 100 milliliters of water, the amount of said hydrocolloid being sufficient to maintain the particles in suspension during said introduction, said dispersion having a viscosity of from 100 to 1500 centipoises; and, after said dispersion has coated the GI tract walls in said region, applying an ultrasonic imaging beam to said region to delineate said walls and structures outside thereof.

9. The method steps of claim 8 in which said clay selected from the group consisting of: kaolin, kaolinite, bentonite, montmorillonite, Fuller's earth, and attapulgite.

10. The method steps of claims 8 or 9 in which said edible clay is kaolin and said hydrocolloid is pectin.

11. The method steps of claims 1, 5 or 8 in which said dispersion is introduced orally and said region to be examined is associated with the stomach and upper colon.

12. The method steps of claims 1, 5 or 8 in which said dispersion is introduced rectally and said region to be examined is associated with the lower colon.

13. The method steps of claims 1, 5 or 8 in which said dispersion contains a degassing agent.

14. The method of claims 1, 5 or 8 in which said dispersion contains polysiloxane degassing agent in an effective amount for promoting degassing of the stomach.

* * * * *